United States Patent
Martinez Palou et al.

(10) Patent No.: US 9,850,197 B2
(45) Date of Patent: Dec. 26, 2017

(54) HALOGEN-FREE IONIC LIQUIDS IN NAPHTHA DESULFURIZATION AND THEIR RECOVERY

(71) Applicant: INSTITUTO MEXICANO DEL PETROLEO, Mexico City (MX)

(72) Inventors: Rafael Martinez Palou, Mexico City (MX); Natalya Victorovna Likhanova, Mexico City (MX); Eugenio Alejandro Flores Oropeza, Mexico City (MX); Diego Javier Guzman Lucero, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 363 days.

(21) Appl. No.: 14/563,159

(22) Filed: Dec. 8, 2014

(65) Prior Publication Data
US 2015/0090639 A1    Apr. 2, 2015

Related U.S. Application Data

(62) Division of application No. 12/548,917, filed on Aug. 27, 2009, now Pat. No. 8,999,151.

(30) Foreign Application Priority Data
Aug. 29, 2008    (MX) .................... MX/a/2008/011121

(51) Int. Cl.
| | |
|---|---|
| C07C 211/64 | (2006.01) |
| C10G 21/20 | (2006.01) |
| C07C 211/62 | (2006.01) |
| C10G 21/12 | (2006.01) |
| C10G 21/16 | (2006.01) |
| C10G 21/27 | (2006.01) |
| C10G 21/28 | (2006.01) |
| B01D 11/04 | (2006.01) |
| C10G 29/20 | (2006.01) |

(52) U.S. Cl.
CPC ........ *C07C 211/64* (2013.01); *B01D 11/0492* (2013.01); *C07C 211/62* (2013.01); *C10G 21/12* (2013.01); *C10G 21/16* (2013.01); *C10G 21/20* (2013.01); *C10G 21/27* (2013.01); *C10G 21/28* (2013.01); *C10G 29/20* (2013.01); *C10G 2300/104* (2013.01); *C10G 2300/1044* (2013.01); *C10G 2300/1051* (2013.01); *C10G 2300/1055* (2013.01); *C10G 2300/202* (2013.01); *C10G 2400/02* (2013.01); *C10G 2400/04* (2013.01)

(58) Field of Classification Search
CPC ....................... C07C 211/62–211/64
See application file for complete search history.

(56) References Cited

U.S. PATENT DOCUMENTS

| | | | |
|---|---|---|---|
| 4,212,729 A | 7/1980 | Hensley, Jr. et al. | |
| 4,752,376 A | 6/1988 | Pachano et al. | |
| 5,730,860 A | 3/1998 | Irvine | |
| 5,910,440 A | 6/1999 | Grossman et al. | |
| 6,171,478 B1 | 1/2001 | Cabrera et al. | |
| 6,749,336 B2* | 6/2004 | Wu .......................... | G01K 5/12 374/190 |
| 7,553,406 B2 | 6/2009 | Wasserscheid et al. | |
| 2002/0035306 A1 | 3/2002 | Gore et al. | |
| 2003/0085156 A1 | 5/2003 | Schoonover | |
| 2004/0045874 A1 | 3/2004 | Olivier-Bourbigou et al. | |
| 2005/0010076 A1 | 1/2005 | Wasserscheid et al. | |
| 2006/0287521 A1 | 12/2006 | Davis | |
| 2009/0163349 A1 | 6/2009 | Elomari et al. | |

FOREIGN PATENT DOCUMENTS

| | | |
|---|---|---|
| EP | 1057879 | 6/2000 |
| WO | 0234863 | 5/2002 |
| WO | 03037835 | 5/2003 |

OTHER PUBLICATIONS

Zaczepinski, S., Exxon Diesel Oil Deep Desulfurization (DODD), Handbook of Petroleum Refining Processes, Editor R.A. Meyer, McGraw-Hill, NY, 1996.
Ito et al, On novel processes for removing sulphur from refinery streams, Catalysis Today 116 (2006) 446-460.
Brunet et al, On the hydrodesulfurization of FCC gasoline: a review, Applied Catalysis A: General 278 (2005) 143-172.
PEP Review Dec. 2001, S Zorb Diesel Sulfur Removal Technology, Richard H. Nielsen, Published Jul. 2003.
Visser et al, Room temperature ionic liquids as replacements for traditional organic solvents and their applications towards green chemistry in separation processes, Rogers et al. (eds), Green Industrial Applications of Ionic Liquids, 137-156, 2003.
Levy et al, AM-01-10 Unipure's ASR-2 Diesel Desulfurization Process: A Novel, Cost-Effective Process for Ultra-Low Sulfur Diesel, 2001.
Cullen et al., AM-01-55 SulphCo—desulfurization via selective oxidation pilot plant results and commercialization plans, NPRA Annual Meeting, Mar. 2001.
Collins et al, Oxidative desulphurisation of oils via hydrogen peroxide and heteropolyanion catalysis, Journal of Molecular Catalysis A: Chemical 1 17 (1997) 397-403.

(Continued)

*Primary Examiner* — Renee Robinson
(74) *Attorney, Agent, or Firm* — Dickinson Wright PLLC

(57) ABSTRACT

Ionic liquids of the general formula $C^+A^-$ where $C^+$ represents an organic cation, specifically, but not limited to the imidazolium, pyridinium, isoquinolinium, ammonium types, which have aliphatic and aromatic substituents, while $A^-$ represents a carboxylate, aromatic and aliphatic anion. The ionic liquids are synthesized under conventional heating or microwave irradiation This invention is also related to the application of ionic liquids to remove sulfur compounds of naphthas through a liquid-liquid extraction and the recovery and reuse of ionic liquids by the application of heat, reduced pressure and washing with solvents.

3 Claims, No Drawings

(56) References Cited

OTHER PUBLICATIONS

Babich et al, Science and technology of novel processes for deep desulfurization of oil refinery streams: a review, Fuel 82 (2003) 607-631.
Lo et al, One-pot desulfurization of light oils by chemical oxidation and solvent extraction with room temperature ionic liquids, Green Chemistry, 2003, 5, 639-642.
Wasserscheid et al (Eds.), Ionic Liquids in Synthesis, Wiley-VCH, Wenheim, 2004.
Zhao et al, Aldrichimica Acta, vol. 35, No. 3, 75-83, 2002.
Rogers et al (Eds.), Ionic Liquids: Industrial Applications of Green Chemistry, ACS, Boston, 2002.
Rogers et al (Eds.), Ionic Liquids as Green Solvent: Progress and Prospects, (ACS Symposium Series), Boston, 2003.
Rogers et al (Eds.), Ionic Liquids IIIB: Fundamentals, Progress, Challenges, and Opportunities: Transformations and Processes (ACS Symposium Series), Boston, 2005.
Rogers et al(Eds.), Green Industrial Applications of Ionic Liquids. (NATO Science Series), Kluwer Academic Publishers, Dordrecht, Netherlands, 2002.
Bosmann et al, Deep desulfurization of diesel fuel by extraction with ionic liquids, Chem. Commun., 2001, 2494-2495.
Huang et al, Desulfurization of Gasoline by Extraction with New Ionic Liquids, Energy & Fuels 2004, 18, 1862-1864.
Zhang et al, Extractive Desulfurization and Denitrogenation of Fuels Using Ionic Liquids, Ind. Eng. Chem. Res. 2004, 43, 614-622.
Murugesan et al, Benzoate-based room temperature ionic liquids—thermal properties and glycosaminoglycan dissolution, Carbohydrate Polymers 63 (2006) 268-271.
Brindaban et al, Ionic Liquid as Catalyst and Reaction Medium. The Dramatic Influence of a Task-Specific Ionic Liquid, [bmlm]OH, in Michael Addition of Active Methylene Compounds to Conjugated Ketones, Carboxylic Esters, and Nitriles, Organic Letters, 2005, vol. 7, No. 14, 3049-3052.

* cited by examiner

HALOGEN-FREE IONIC LIQUIDS IN NAPHTHA DESULFURIZATION AND THEIR RECOVERY

CROSS-REFERENCE TO RELATED PATENT APPLICATION

This application is a divisional application of Ser. No. 12/548,917, filed Aug. 27, 2009, which claims the benefit under 35 U.S.C. §119 of Mexican Patent Application No. MX/a/2008/011121, filed on Aug. 29, 2008, in the Mexican Patent Office, the disclosures of which are hereby incorporated by reference in their entirety.

FIELD OF THE INVENTION

The present invention is related to the synthesis of new halogen-free ionic liquids which are insoluble in hydrocarbon mixtures and with the property of dissolving aliphatic and aromatic sulfur-containing compounds that contaminate the naphtha. In accordance with the present invention a desulfurization process is carried out by a liquid-liquid extraction process at room temperature and pressure.

Specifically, the invention is related to the synthesis of halogen-free ionic liquids and their application to remove sulfur-containing compounds, in which ionic liquids are provided which have the general formula $C^+ A^-$, where $C^+$ represents an organic cation, especially but not exclusively of: alkylpyridinium, dialkylimidazolium, trialkylimidazolium, tetraalkylammonium and alkylquinolinium types, while the anion $A^-$ represents carboxylate organic derivatives of aliphatic and aromatic carboxylic acids, such as acetate, butanoate, stearate and benzoate, among others. Additionally, the invention covers the regeneration and reuse of these ionic liquids by means of heating, reduced pressure and washing with solvents.

BACKGROUND OF THE INVENTION

The gases emitted by internal combustion engines represent the main source of atmospheric pollution and depend directly on the quality of the combustible used. Different actions have been carried out worldwide for the production and refining of higher quality gasoline and diesel. For example, since 2005 the European Union set the upper limit of 50 ppm of sulfur in diesel and gasoline; however Germany has gone further and reduced to 10 ppm. For the United States of America the standard for the maximum content of sulfur in gasoline will be 80 ppm and 30 ppm as average. In Mexico, PEMEX (Pemex Refining), based on their commitment to producing and distributing gasoline to comply with environmental laws and international standards of quality, is adjusting its parameters to produce gasoline, as a rule establishing maximum sulfur content between 15 and 30 ppm from 2008 until 2010.

The most used treatment for desulfurization of gasolines in refining processes is catalytic hydrodesulfurization at high temperature and pressure (HDS process) (I. Pachano, J. Guitian, O. Rodríguez, J. H. Krasuk (Intevep. S. A.) U.S. Pat. No. 4,752,376 (1988), Jr. Hensley, L. Albert, L. M. Quick, (Standard Oil Company) U.S. Pat. No. 4,212,729); however this process is very expensive and drastic conditions of operation are required, employing transition metal-containing catalyst, which lose their activity quickly, especially for heavy Mexican oils with higher content of sulfur, which are very difficult for processing and for sulfur removal.

In some countries new Technologies have been developed for resolving this problem (Zaczepinski, S. *Exxon Diesel Oil Deep Desulfurization (DODD)* in *Handbook of Petroleum Refining Processes*, ed. R. A. Meyer, McGraw-Hill, NY, 1996, Cap. 8.7; Ito, E.; Rob, J. A.; Veen, R. V. *Catal. Today* 2006, 116, 446-460; Brunet, S.; Mey, D.; Pérot, G.; Bouchy, C.; Diehl, F. *Appl. Catal. A* 2005, 278, 143-172) for example the adsorption of sulfur compounds under solid absorbent, this process is known as IRVAD® (U.S. Pat. No. 5,730,860, dated 1998-03-24) from Black & Veatch Pritchard Inc., the process S Zorb® from Phillips Petroleum (http://www.eia-.doe.gov/oiaf/servicerpt/ulsd/uls.html) and the process from Haldor Topsoe (EP 1057879, published date: 2000 Dec. 6); the liquid-liquid extractions with common organic solvents (Petrostar Refining, 217 National Meeting, American Chemical Society, Anaheim, Calif., March 1999) oxidative desulfurization with different oxidant agents (Unipure Corp., NPRA Meeting No AM-01-10, March 2001; Sulphco Corp, NPRA Meeting No AM-01-55, March 2001; BP Chemicals UK, Journal of Molecular Catalysis A: Chemical (1997) 397-403; UOP LLC, U.S. Pat. No. 6,171,478 dated 2001 Jan. 9; EXXON Research and Engineering Co., U.S. Pat. No. 5,910,440 dated 1999 Jun. 8, U.S. Patent Publication No. 2002/35306A1 dated 2002 Mar. 21; *Fuel* 2003, 82, 4015; *Green Chem.* 2003, 5, 639).

Ionic liquids have attracted the attention of research due to their physicochemical properties, such as: very low vapor pressure, non-flammability, non-corrosives, low toxicity and by these reason they are excellent substitutes of common volatile organic solvents (Wasserscheid, P.; Keim, W. (Eds.) *Ionic Liquids in Synthesis*, Wiley-VCH, Wenheim, 2004; Welton, T. *Chem. Rev.* 1999, 99, 2071-2084; Zhao, H.; Malhotra, S. V. *Aldrichimica Acta* 2002, 35, 75-83) and promote their application in different oil refining processes and for chemical industry (Rogers, R. D.; Seddon, K. R (Eds.) *Ionic Liquids: Industrial Applications of Green Chemistry*. ACS, Boston, 2002; Rogers, R. D.; Seddon, K. R (Eds.) *Ionic Liquids as Green Solvent: Progress and Prospects*. (ACS Symposium Series), Boston, 2003; Rogers, R. D.; Seddon, K. R (Eds.) *Ionic Liquids IIIB: Fundamentals, Progress, Challenges, and Opportunities: Transformations and Processes* (ACS Symposium Series), Boston, 2005; Roger, R. D.; Seddon, K. R.; Volkov, S (Eds.). *Green Industrial Applications of Ionic Liquids*. (NATO Science Series), Kluwer Academic Publishers, Dordrecht, Netherlands, 2002).

One of the first publications that mention the use of ionic liquid for removing mercaptans from hydrocarbon fluid is WO Publication No. 0234863 with publication date 2002 May 2. The methods described are based on the use of sodium hydroxide in combination of ionic liquids to favor the conversion of mercaptans in mercaptides, which are removed with ionic liquids. During the 2005-2009 years, Peter Wasserscheid and coworkers have published several patents and papers about the ionic liquids for the process of the deep desulfurization of hydrocarbons (Chem. Com. (2001) 2494; WO 03037835 published 2003 May 8, U.S. Patent Publication No. 2005/0010076A1, published 2005-01-13). In these works the author employed ionic liquids with general formula $C^+A^-$ where $C^+$ is 1,3-dialkyllimidazolium or tetraalkylammonium and $A^-$ are tetrachloroaluminates or methanesulfonates. By means of a process with several and successive extractions (up to 8 extractions), high sulfur extraction efficiencies were achieved using model gasolines. However, the use of ionic liquids containing aluminum salts have the problem of the high acidity of chloroaluminates which leads to secondary reactions such as olefins polymerization, in addition ionic liquids containing this anion type are highly hygroscopic and non-stables to atmospheric humidity.

U.S. Patent Publication No. 2003/0085156A1, published 2003 May 8, also makes mention of the use of ionic liquids where the quaternary ammonium or alkylphosphonium are the cations and tetrachloroaluminate as anion. For the extraction of sulfur compounds in synthetic fuels, it is mentioned that these compounds can be oxidized to sulfoxides or sulfones before or during the extraction process.

It was published in Energy & Fuels 18 (2004) 1862, that CuCl-based ionic liquids exhibited desulfurization ability of gasoline when used in an extraction process; as well as a published paper (Zhang, S.; Zhang, Q.; Conrad Zhang, Z. Ind. Eng. Chem. Res. 43 (2004) 614) some ionic liquids properties and sulfur and nitrogen compounds removal from transportation fuels were studied.

In U.S. Patent Publication No. 2004/0045874A1, published 2004 Mar. 11, a process for desulfurization and denitrogenation of hydrocarbon fractions using a wide family of ionic liquids was explored with alkylating agents of high efficiencies.

SUMMARY OF THE INVENTION

All above mentioned references are overcome by the present invention, because none of them claimed the use of ionic liquids containing aliphatic or aromatic carboxylate anions, which has the advantage that it does not decompose during the desulfurization process and can be regenerated and reutilized in several consecutive extraction processes. Another object of the present invention is the utilization of these ionic liquids in the deep desulfurization of organic liquids and naphtha by a selective extraction of organosulfur compounds. It is important to mention that the term naphtha refers to a petroleum fraction constituted by organosulfur compounds from $C_4$-$C_9$, with a concentration of 85-90% in weight, density of 0.64-0.85 g/cm$^3$, preferably of 0.64-0.70 g/cm$^3$, 30-220° C., preferably of 30-140° C., and a content of total sulfur of 100-500 ppm, preferably of 100-250 ppm.

Syntheses of ionic liquids of the present invention were carried out in two steps, in the first step, an alkyl, alkenyl, benzyl or alkyl-functionalized halides (both chlorides and bromides) were placed to react with alkenyl, benzyl, or alkyl functionalized imidazoles, pyridines, isoquinoline or tertiary amines, while in the second step, anion interchange reaction happened between the ionic liquid with a silver carboxylate.

On the other hand, for the removal of sulfur compounds, a liquid-liquid extraction is made, which the ionic liquid naphtha is mixed with naphtha and is subjected to agitation, and then separates the two phases: desulfurized naphtha and the sulfured ionic liquid.

The present invention also encompasses a procedure for recovering the ionic liquids in order that they can be used again to remove sulfur compounds, this procedure involves three stages: the first provides heating at reduced pressure, in the second, they are performed washings with organic solvents, and in the third, such solvents are removed under vacuum conditions.

DETAILED DESCRIPTION OF THE INVENTION

The present invention is related to the synthesis and application of ionic liquids that have kind of carboxylate anions and are halogen-free and remove efficiently sulfur compounds contaminants from naphtha.

The process of extraction and removal of sulfur compounds from a sulfur containing liquid is composed of the strong agitation of the two phases (ionic liquids and naphtha) followed by a process of separation of phases, where the sulfur compounds pass to phase comprising the ionic liquid and as a result total sulfur content is considerably reduced in the naphtha, this occurs due to the higher affinity of sulfur compounds into the ionic liquid compared with naphtha.

Ionic liquids used in the present invention have general formula $C^+$ $A^-$ where $C^+$ is an organic cation such as imidazolium, pyridinium, isoquinolinium and ammonium, and $A^-$ is an anion-type organic carboxylate, including aromatic and aliphatic substituents as shown in Table 1.

TABLE 1

Overall structure of cations and anions constituting the ionic liquids of this invention $C^+$ (Cations)

Imidazolium

Pyridinium

Isoquinolinium

Quaternary ammonium $A^-$ (Anions)

Carboxylate where: R, $R_1$, $R_2$ y $R_3$ are independently radicals represented by alkyl group, cycloalkyl group, alkenyl group, benzylic group and alkyl functionalized group, preferably these groups have from 1 to 10 carbon atoms; $R_4$ comprises alkyl group, cycloalkyl group, alkenyl group, benzylic group and alkyl functionalized group, preferably these groups have from 1 to 18 carbon atoms.

In one aspect of the invention, a process for the desulfurization of an organic liquid includes the steps of contacting the organic liquid with the ionic liquid having the formula $C^+$ $A^-$, where $C^+$ and $A^-$ are as defined above. The desulfurization is carried out by a liquid-liquid extraction where the sulfur compounds are recovered in the ionic liquid. The ionic liquid is immiscible with the organic liquid which results in a phase separation. The organic liquid can be, for example, naphtha, as defined above, gasoline, diesel fuel, kerosene, heating oil and other petroleum based liquids.

EXAMPLES

Synthesis of Ionic Liquids of this Invention

Synthesis of halogen-free ionic liquids of this invention was conducted in the following two stages using the methods described in the literature (Saravanabubu M, Wiencek J M, Ren R X, Linhardt R J. *Carbohydr. Polymer* 63 268-271 (2006); Brindaban C R and Subas B. *Org. Lett.* 7 3049-3052 (2005).

First Step. Ionic liquid was synthesized by reaction of alkyl, alkenyl, benzyl or alkyl-functionalized chlorides and bromides, with organic nitrogen compounds such as imidazole, pyridine, isoquinoline and tertiary amines.

Second step. An anion exchange performed by the reaction of the respective ionic liquid with a silver carboxylate, resulting in a silver halide which precipitates and is separated from the reaction by filtration Both steps were prepared using both conventional heating and microwave oven; the last heating method produces ionic liquids with higher yields (5 to 9%) and in shorter times (95 to 99%) than the first one.

The syntheses of the present invention are illustrated by the preparation of eight ionic liquids named LI 1, LI 2, LI 3, LI 4, LI 5, LI 6, LI 7 y LI 8 respectively, but it does not mean some restriction. The preparation procedure is exemplified by the synthesis of 1-hexyl-3-methyl-imidazolium acetate (LI-1), using two different methods, conventional and microwave heating.

Example 1

Synthesis of 1-hexyl-3-methyl-imidazolium Acetate (LI-1)

Method 1 Conventional Heating

First step: An oven-dried, 100-mL, three-necked, round bottomed flask equipped with a magnetic stirring bar, thermometer and a reflux condenser is charged with 20 mmol 1-methyl-imidazole and 60 mmol of 1-bromohexane, the resulting solution was heated at 80° C. for 24 hr. At the end of this time, two phases were produced, the upper phase was decanted and the lower phase, which contained the ionic liquid, was washed with ethyl acetate (3×20-mL). The solvent was eliminated at reduced pressure.

Second step (Anion interchange): An oven-dried, 100-mL, three-necked, round bottomed flask equipped with a magnetic stirring bar, thermometer and a reflux condenser, were dissolved 10 mmol of 1-hexyl-3-methyl-imidazolium bromide obtained in first step, in 50-mL of acetonitrile. Silver acetate (10 mmol) was slowly added to the solution. The mixture was refluxed for 10 hr, and then the precipitated was filtered off, the ionic liquid was dried under vacuum conditions and it was obtained a yellow liquid.

Synthesis of 1-hexyl-3-methyl-imidazolium Acetate (LI-1)

Method 2: Microwave Heating

First step: An oven-dried, 100-mL, one-necked, round bottomed flask equipped with a magnetic stirring bar, and a reflux condenser is charged with 20 mmol of 1-methyl-imidazole and 60 mmol of 1-bromohexane, the resulting solution was exposed to microwave irradiation in a CEM Discover Labmate microwave oven (100 watts power) and heated at 80° C. for 10 min. At the end of this time, two phases were produced, the upper phase was decanted and the lower phase, which contained the IL, was washed with ethyl acetate (3×20-mL). The solvent was eliminated at reduced pressure.

Second step (Anion interchange): An oven-dried, 100-mL, one-necked, round bottomed flask equipped with a magnetic stirring bar, and a reflux condenser, were dissolved 10 mmol of 1-hexyl-3-methyl-imidazolium bromide obtained in first step, in 50-mL of acetonitrile. Silver acetate (10 mmol) was slowly added to the solution. The mixture was heated in a CEM Discover Labmate microwave oven (75 watts power) for 12 min; silver bromide was filtered off, the ionic liquid was dried under vacuum conditions and it was obtained a yellow liquid.

Examples 2 to 8

The ionic liquids of this invention were synthesized using two different heating methods, the first one (conventional heating) and the second one (microwave heating). The interchange anion step was done using silver carboxylate (acetate, benzoate, butanoate and stearate). The ionic liquids of this invention were characterized by spectroscopic $^1$H and $^{13}$C Nuclear Magnetic Resonance data, the chemical shifts are reported in ppm in $d_6$-DMSO and $CDCl_3$ with tetramethylsilane as an internal Standard.

The spectroscopic data and yields of the ionic liquids synthesized in this invention are summarized as follows:

Yields and spectroscopic data of ionic liquids (1 to 8)

Ionic Liquid 1 (LI-1)

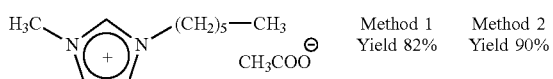

| | Method 1 | Method 2 |
|---|---|---|
| | Yield 82% | Yield 90% |

Example 1

1-hexyl-3-methyl-imidazolium acetate
$^1$H NMR (DMSO-$d_6$) δ 0.82 (t, J = 6.9 Hz, 3H), 1.22 (m, 6H), 1.75 (sx, J = 5.6 Hz, 2H), 1.80 (s, 3H), 3.87 (s, 3H), 4.18 (t, J = 7.1 Hz, 2H), 7.78 (dd, $J_1$ = 1.6 Hz, $J_2$ = 1.9 Hz, 1H), 7.87 (dd, $J_1$ = 1.6 Hz, $J_2$ = 1.9 Hz, 1H), 9.39 (s, 1H) ppm. $^{13}$C NMR (DMSO-$d_6$) δ 14.3, 22.4, 22.9, 25.7, 29.9, 31.1, 36.3, 49.3 122.8, 124.1, 137.2, 173.5 ppm.

Ionic Liquid 2 (LI-2)

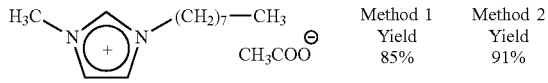

| | Method 1 | Method 2 |
|---|---|---|
| | Yield 85% | Yield 91% |

Example 2

1-octyl-3-methyl-imidazolium acetate
$^1$H NMR DMSO-$d_6$) δ 0.82 (t, J = 6.9 Hz, 3H), 1.24 (m, 10H), 1.82 (sx, J = 6.8 Hz, 2H), 2.04 (s, 3H), 3.85 (s, 3H), 4.15 (t, J = 7.0 Hz, 2H), 7.42 (dd, $J_1$ = 5.5, 1.1 Hz, 2H), 8.69 (s, 1H) ppm. RMN $^{13}$C (75.4 MHz, DMSO-$d_6$) δ 13.6, 22.2, 22.7, 25.5, 28.3, 28.4, 29.4, 31.2, 35.9, 49.8, 122.4, 122.7, 137.0, 175.0 ppm.

Ionic Liquid 3 (LI-3)

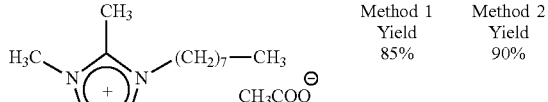

| | Method 1 | Method 2 |
|---|---|---|
| | Yield 85% | Yield 90% |

Example 3

1,2-dimethyl-3-octyl-imidazolium acetate
$^1$H NMR($CDCl_3$) δ 0.87 (t, J = 6.6 Hz, 3H), 1.26 (m, 10H), 1.81 (sx, J = 7.0 Hz, 2H), 2.04 (s, 3H), 2.78 (s, 3H), 3.99 (s, 3H), 4.18 (t, J = 7.4 Hz, 2H), 7.45 (d, J = 2.0 Hz, 1H), 7.67 (d, J = 2.0 Hz, 1H) ppm. RMN $^{13}$C (75.4 MHz, $CDCl_3$) δ 10.3, 13.6, 21.4, 22.2, 25.9, 28.6 (2C), 29.5, 31.3, 35.6, 48.6, 120.9, 122.7, 143.4, 175.2 ppm.

Yields and spectroscopic data of ionic liquids (1 to 8)

Ionic Liquid 4 (LI-4)

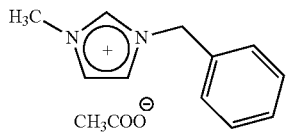

| Method 1 Yield | Method 2 Yield |
|---|---|
| 89% | 95% |

Example 4

1-benzyl-3-methyl-imidazolium acetate
$^1$H RMN (CDCl$_3$) δ 1.98 (s, 3H), 4.02 (s, 3H), 5.52 (s, 2H), 7.33-7.51 (m, 7H), 10.43 (s, 1H) ppm. RMN $^{13}$C (75.4 MHz, CDCl$_3$) δ 22.6, 36.5, 53.2, 121.8, 123.7, 128.8 (2C), 129.4 (3C), 133.4, 138.2, 175.6 ppm.

Ionic Liquid 5 (LI-5)

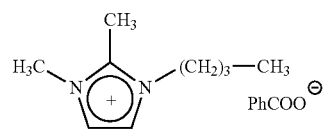

| Method 1 Yield | Method 2 Yield |
|---|---|
| 89% | 95% |

Example 5

1,2-dimethyl-3-butyl-imidazolium benzoate
$^1$H RMN (CDCl$_3$) δ 0.82 (t, J = 7.2 Hz, 3H), 1.20 (sx, J = 7.6 Hz, 2H), 1.55 (qi, J = 7.4 Hz, 2H), 2.47 (s, 3H), 3.71 (s, 3H), 3.87 (t, J = 7.4 Hz, 2H), 7.22-7.32 (m, 5H), 7.97 (dd, J$_1$ = 8.2, 1.6 Hz, 2H) ppm. RMN $^{13}$C (75.4 MHz, CDCl$_3$) δ 9.6, 13.4, 19.5, 31.6, 35.3, 48.3, 121.0, 123.1, 127.6, 129.5, 130.1, 137.3, 143.3, 171.1 ppm.

Ionic Liquid 6 (LI-6)

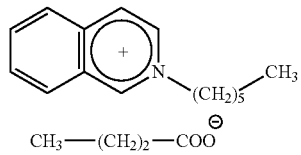

| Method 1 Yield | Method 2 Yield |
|---|---|
| 83% | 91% |

Example 6

Butyl-isoquinolinium butanoate
$^1$H RMN (CDCl$_3$) δ 0.82 (t, J = 7.5 Hz, 3H), 0.95 (t, J = 7.2 Hz, 3H), 1.30 (m, J = 7.6 Hz, 6H), 1.7 (m, J = 7.2 Hz, 2H), 2.1 (t J = 6.0 Hz, 2H), 2.3 (t, J = 7.2 Hz, 2H), 5.0 (t, J = 6.0 Hz, 2H), 7.5-7.86 (m, 5H), 8.5 (s, 1H), 9.15 (s, 1H) ppm. RMN $^{13}$C (75.4 MHz, CDCl$_3$) δ 13.8, 14.1, 18.6, 22.3, 25.9, 28.8, 31.1, 36.1, 61.9, 120.4, 126.4, 127.15, 128.63, 130.2, 135.7, 142.9, 152.4, 173.8 ppm Ionic Liquid 7 (LI-7)

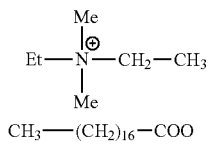

| Method 1 Yield | Method 2 Yield |
|---|---|
| 78% | 89% |

Example 7

Dimethyl-diethyl-ammonium stearate
$^1$H RMN (CDCl$_3$) δ 0.9 (s, 3H), 1.39 (t, J = 7.26 Hz, 6H), 1.5 (m, 28H), 1.6 (m, 2H), 2.28 (m, 2H), 2.92 (s, 6H), 3.34 (c, J = 7.14 Hz, 4H), ppm. RMN $^{13}$C (75.4 MHz, CDCl$_3$) δ 7.8, 14.1, 22.7, 25.0, 29.3, 29.7, 32.0, 34.1, 49.16, 60.1, 174.8 ppm Ionic Liquid 8 (LI-8)

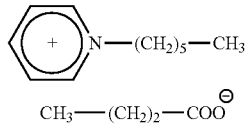

| Method 1 Yield | Method 2 Yield |
|---|---|
| 83% | 91% |

Example 8

Butyl-pyridinium butanoate
$^1$H RMN (CDCl$_3$) δ 0.86(t, J = 7.5 Hz, 3H), 0.95 (t, J = 7.2 Hz, 3H), 1.24 (m, J = 7.6 Hz, 6H), 1.7 m, J = 7.2 Hz, 2H), 2.15 (t J = 6.0 Hz, 2H), 2.4 (t, J = 7.2 Hz, 2H), 5.2 (t, J = 6.0 Hz, 2H), 8.23 (t, J = 6.0 Hz, 2H), 8.61 (t, J = 6.0 Hz, 1H), 9.62 (d, J = 6.0 Hz, 2H) ppm. RMN $^{13}$C (75.4 MHz, CDCl$_3$) δ 13.5, 13.8, 18.9, 21.3, 25.5, 28.8, 31.2, 36.1, 63.8, 128.5, 145.2, 177.6 ppm Example 9

Extraction of Sulfured Compounds from Naphtha

The procedure for the sulfured compound removal of the naphtha consisted of putting in contact one part of ionic liquid with 10 parts of naphtha (w/w) whose sulfur content has been determined previously. The mixture is shaken vigorously during 10 minutes, the two phases are separated and the sulfur content is determined in the naphtha after the extraction to determine the percentage of total sulfur removal. The determination of the sulfur content was carried out by method ASTM-D 5453-05: Standard Test for Method Determination of Total Sulfur in Light Hydrocarbons, Fuels Motor and Oils by Ultraviolet Fluorescence.

The percentage of sulfur removed after the extraction liquid-liquid is shown in Table 2.

TABLE 2

Total sulfur removed

| Ionic liquid | % of total sulfur removed of the gasoline |
|---|---|
| LI-1 | 68 |
| LI-2 | 72 |
| LI-3 | 68 |
| LI-4 | 70 |
| LI-5 | 67 |
| LI-6 | 66 |
| LI-7 | 69 |
| LI-8 | 68 |

Total sulfur in the natural gasoline: 210 ppm
Note:
LI-1 = 1-hexyl-3-methyl-imidazolium acetate
LI-2 = 1-Octyl-3-methyl-imidazolium acetate
LI-3 = 1,2-dimethyl-3-octyl-imidazolium acetate
LI-4 = 1-benzyl-3-methyl-imidazolium acetate
LI-5 = 1,2-dimethyl-3-butyl-imidazolium benzoate
LI-6 = Butyl-isoquinolinium butanoate
LI-7 = Dimethyl-diethyl ammonium stearate
LI-8 = Butyl-pyridinium butanoate From the Table No 2 is come off that the greater extraction sulfured compounds to start off of naphtha, was made with 1-octyl-3-methyl-imidazolium acetate (Ionic liquid, LI-2). The tests of recovery and recycling were made with this compound.

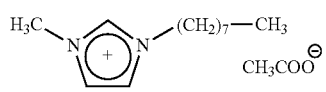

LI-2

1-Octyl-3-methyl-imidazolium acetate

Example 10

Recovering and Recycling of the Ionic Liquids

After each extraction the regeneration of the ionic liquids was realized by a procedure which consists of three steps; in the first step the ionic liquid was heated between 60 and 90° C., preferably of 75 to 85° C., in conditions of reduced pressure between 130 and 150 mmHg, preferably from 135 to 145 mmHg, for elimination of volatile compounds, in the second step, the ionic liquid was washed with solvents as ether, hexanes, heptanes, ether of petroleum or using mixtures of them in a proportion v/v between 1 and 15, preferably from 1 to 10; and in the third step the solvent was eliminated under vacuum.

The Table 3 shows the results of the sulfur removal after 3 cycles of regeneration and recycling of the LI-2, using original naphtha in each cycle.

TABLE 3

Desulfurization of original naphtha using recovered ionic liquid.

| Ionic liquid IL-2 | Extraction cycle | Sulfur removal (%) |
|---|---|---|
| H₃C—N(+)=N—(CH₂)₇—CH₃  CH₃COO⁻ | 1 | 72 |
|  | 2 | 70 |
|  | 3 | 67 |

1-octyl-3-methyl-imidazolium acetate

As listed in Table 3, the ionic liquids can be used several times in removing sulfur compounds, because the performance of sulfur removing is very similar, indicating that they do not lose their physicochemical characteristics during the extraction process and recovery Quantitative desulfurization of naphtha was accomplished in three consecutives cycles of extraction (over 95%), using the ionic liquids described in this invention, as shown in Table 4.

TABLE 4

Total sulfur removed using the desulfurated naphtha of previous extraction

| Ionic liquid IL-2 | Extraction cycle | Sulfur removal (%) |
|---|---|---|
| H₃C—N(+)=N—(CH₂)₇—CH₃  CH₃COO⁻ | 1 | 72 |
|  | 2 | 87 |
|  | 3 | 96 |

1-octyl-3-methyl-imidazolium acetate

In Table 4 shown that with increasing the number of extraction cycles, increases the removal of sulfur, reaching values very close to the total extraction (100%).

While various embodiments have been chosen to illustrate the invention, it will be understood that various changes and modifications can be made without departing from the scope of the invention as recited in the appended claims.

What is claimed is:

1. An ionic liquid containing a heterocyclic cation and a carboxylate anion and having the formula $C^+A^-$ wherein
   $C^+$ is an isoquinolinium cation, and
   $A^-$ is a carboxylate anion having the formula

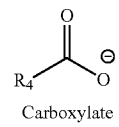

Carboxylate where $R_4$ is selected from the group consisting of cycloalkyl, alkenyl, and benzylic.

2. The ionic liquid of claim 1, wherein said heterocyclic cation is an isoquinolinium cation having at least one substituent selected from the group consisting of benzylic, cycloalkyl, and alkenyl having 1 to 10 carbon atoms.

3. The ionic liquid of claim 1, wherein said isoquinolinium cation has the formula

Isoquinolinium where R is selected from the group consisting of alkyl, cycloalkyl, alkenyl, benzylic, and functionalized alkyl having 1 to 10 carbon atoms.

* * * * *